United States Patent [19]

Krämer et al.

[11] 4,028,409
[45] June 7, 1977

[54] PROCESS FOR THE PREPARATION OF α-OXOTHIODIMETHYLAMIDE COMPOUNDS

[75] Inventors: Wolfgang Krämer; Wilfried Draber; Helmut Timmler; Heinz Förster, all of Wuppertal, Germany

[73] Assignee: Bayer Aktiengesellschaft, Leverkusen, Germany

[22] Filed: Dec. 15, 1975

[21] Appl. No.: 640,829

[30] Foreign Application Priority Data

Dec. 21, 1974 Germany .................. 2460909

[52] U.S. Cl. ............................................. 260/551 S
[51] Int. Cl.² ............. C07C 153/05; C07C 153/057
[58] Field of Search ................................. 260/551 S

[56] References Cited

UNITED STATES PATENTS

| 2,456,785 | 12/1948 | King | 260/551 S X |
| 2,459,706 | 1/1949 | King | 260/551 S X |
| 2,689,246 | 9/1954 | Feichtinger | 260/551 S X |

FOREIGN PATENTS OR APPLICATIONS

| 1,270,552 | 6/1968 | Germany | 260/551 S |

OTHER PUBLICATIONS

Asinger et al., CA 64:17576c – 17578f (1966).
Asinger et al., CA 59:1620c – 1621h (1963).
Matsuda et al., CA 78:110804h (1973).

Primary Examiner—Daniel E. Wyman
Assistant Examiner—Thomas A. Waltz
Attorney, Agent, or Firm—Burgess, Dinklage & Sprung

[57] ABSTRACT

α-Oxothiodimethylamide compounds such as tert.-butyl-glyoxyl acid thiodimethylamide are prepared by reacting an α-chloroketone of the formula

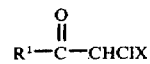

in which
X is hydrogen or chlorine and
R¹ is alkyl or aryl with sulfur and dimethylamine in water at a temperature between 50° and 90° to produce the corresponding α-oxothiodimethylamide of the formula

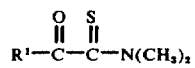

wherein
R¹ is identified above.

12 Claims, No Drawings

PROCESS FOR THE PREPARATION OF α-OXOTHIODIMETHYLAMIDE COMPOUNDS

The present invention relates to a process for the preparation of certain α-oxothiodimethylamide compounds. Such compounds are useful as intermediates in the synthesis of herbicidally active substances. It is known that α-oxothioamides of formulas (II) and (III) as shown below, such as, for example, phenylglyoxyl acid thioamides or tert.-butylglyoxyl acid thioamides are obtained when α-oxodichlorides (I), such as, for example, α,α-dichloroacetophenone or α,α-dichloropinacolone, are reacted with primary or secondary amines and sulfur in ether at temperatures below 40° C (see F. Asinger, A. Saus, H. Offermanns and H.D. Hahn, Liebigs Ann. Chem. 691, (1966), 92–109).

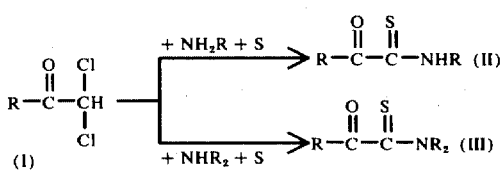

R = alkyl or aryl.

However, this process has a number of disadvantages. Thus, the only solvent expressly described is absolute ether. Moreover, the yields are not very high, especially of the N-di-substituted α-oxothioamides (III).

It is also known that aryl-glyoxyl-thiodimethylamides (V) are prepared when aromatic methyl ketones (IV) are reacted with disulfur dichloride in carbon tetrachloride and the reaction product (a resin of unknown structure), dissolved in dimethylformamide, is treated with dilute aqueous sodium hydroxide solution (see T. Matsuda and Y. Takada, Int. J. Sulfur Chem., A, 2 (1972) No. 2, 89-92).

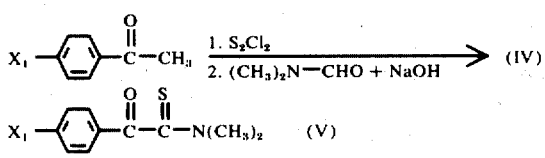

$X_1$ = H, $CH_3O$ or Cl.

This process also has various disadvantages, for instance the use of expensive dimethylformamide, which, as both a reactant and a solvent, must be employed in excess, and also the use of the toxic and unstable disulfur dichloride. Moreover, the yields are not always satisfactory since some of the arylglyoxyl-thiodimethylamides (V) are soluble in the reaction mixture.

The present invention provides a process for the preparation of of an α-oxothiodimethylamide of the general formula

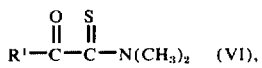

in which
R¹ is alky or aryl,
in which an α-chloroketone of the general formula

in which
X is hydrogen or chlorine, and
R¹ has the above-mentioned meaning,
is reacted with sulfur and dimethylamine in water at temperatures between 50° and 90° C, preferably between 60° and 80° C, partial replacement of dimethylamine by sodium hydroxide solution being possible.

Preferably R¹ is an alkyl radical with 1 to 4 carbon atoms (especially the tert.-butyl radical) or aryl with 6 to 10 carbon atoms (especially phenyl).

It is to be regarded as extremely surprising that, according to the reaction of the invention, water can be used as the solvent since, in the light of that state of the art, it has to be expected that only organic solvents would guarantee a successful course of reaction. It is also surprising that when sodium hydroxide solution is used in part a Willgerodt reaction does not take place, that is to say there is no partial reduction of the keto group.

The process according to the invention has a number of advantages. Thus, the conduct of the reaction and the process engineering are generally greatly facilitated and simplified by the use of water as the solvent. The use of sulfur makes it possible to dispense with the toxic and unstable sulfur dichloride. In contrast to the reaction with organic solvents, the yields are very high, being over 90%.

If α,α-dichloropinacolone, sulfur and dimethylamine are used as the starting materials, the course of the reaction can be represented by the following equation:

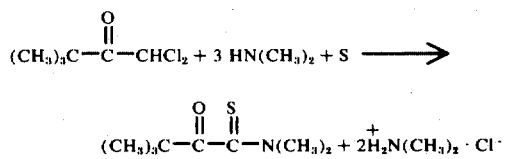

The α-chloroketones of the formula (VII), which can be used according to the invention, are already known (see, inter alia, Beilsteins Handbuch der organischen Chemie (Beilstein'Handbook of Organic Chemistry), main volume I, page 695; supplementary volume III 1, page 2,842; main volume 7, page 282; and supplementary volume III 7, page 972).

When carrying out the process according to the invention 1 mole of sulfur and 3 moles of dimethylamine or 2 moles of sulfur and 2 moles of dimethylamine were preferably employed per mole of the α-chloroketone of the formula (VII), depending on whether X is chlorine or X is hydrogen. The particular stoichiometric excess of amine of 2 moles or 1 mole respectively serves to bind the hydrochloric acid. A further excess can be used, the yield being at a maximum with between 3 and about 5 moles of dimethylamine. It is also possible partially to replace the amine by sodium hydroxide solution.

The sequence in which the reactants were mixed together can be varied.

The α-oxothiodimethylamides, which can be prepared according to the invention, of the formula (VI) can be used as intermediates in the synthesis of herbicidally active substance. For example, 6-tert.-butyl-3-methylthio-4-amino-1,2,4-triazin-5(4H)-one (XI) a compound having a herbicidal action, was obtained from tert.-butylglyoxyl acid thioamide (= trimethylpyruvic acid thiodimethylamide) (VI A) according to the following set of equations (see U.S. Pat. No. 3,671,523):

1st stage

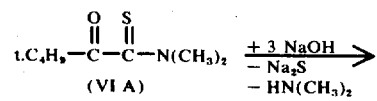

(VI A)

$+ 3 \text{ NaOH}$
$- \text{Na}_2\text{S}$
$- \text{HN(CH}_3)_2$

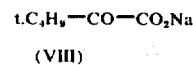

(VIII)

2nd stage (VIII) $\xrightarrow[- \text{NaCl}]{\substack{1) + \text{HCl} \\ 2) + \text{NH}_2-\text{NH}-\overset{\text{S}}{\underset{\|}{\text{C}}}-\text{NH}-\text{NH}_2}}$

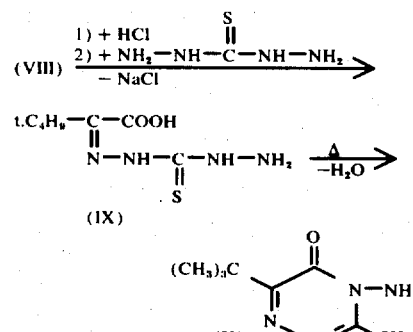

(IX)

(X)

3rd stage

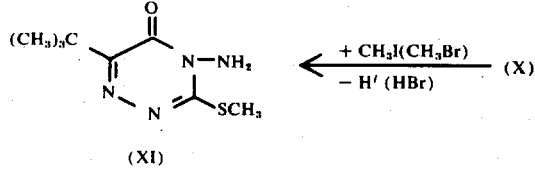

(XI)

This reaction sequence may be effected as follows:

1st stage 3 moles of 45% strength sodium hydroxide solution and at least 200 ml of water were added to 1 mole of thioamide (VI A) and the mixture was left to react for about 4.5 hours at 106°–108° C internal temperature. The Na salt (VIII) can be precipitated almost quantitatively from the aqueous solution by adding sodium hydroxide (in the normal course of reaction it does not need to be isolated).

2nd stage 38 g (0.25 mole) of pure Na salt (VIII), 400 ml of water and 26.6 g (0.25 mole) of thiocarbohydrazide (TCH) were initially introduced. 50 g of half-concentrated hydrochloric acid was added dropwise slowly (about 30 minutes) at −1° to 0° C. The mixture was stirred for a further 0.5 hour and then filtered. 53 g (97% of theory) of compound (IX) of melting point 212°–215° C were obtained. By means of dry heating, this substance can be converted quantitatively into butylthione (= 3-mercapto-4-amino-6-tert.-butyl-1,2,4-triazin-5(4H)-one) (X).

3rd stage 4 parts by weight of butylthione (X) were dissolved in a mixture of 11 parts by weight of 2-normal sodium hydroxide solution and 4 parts by weight of methanol and the solution was treated at 0° C with 3.2 parts by weight of methyl iodide. The reaction mixture was then stirred for a further 4 hours at 20° C. The reaction product crystallized out and was filtered off, dried and recrystallized from benzene. 3.52 parts by weight (82% of theory) of 3-methylthio-4-amino-6-tert.-butyl-1,2,4-triazin-5(4H)-one (XI) of melting point 126°–127° were obtained.

A further herbicidal compound, 4-amino-3-methyl-6-phenyl-1,2,4-triazin-5(4H)-one, (see German Published Specification 2,224,161), was obtained starting from phenylglyoxyl acid thioamide (VI B) according to the following set of equations:

1st stage

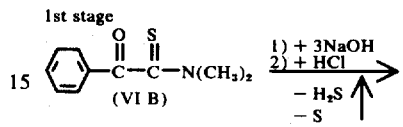

(VI B)

1) + 3NaOH
2) + HCl
$- \text{H}_2\text{S} \uparrow$
$- \text{S}$

⌬—CO—COOH
(XII)

2nd stage (XII) $\xrightarrow[- \text{H}_2\text{O}]{+ \text{CH}_3\text{OH}}$ ⌬—CO—CO$_2$CH$_3$
(XIII)

3rd stage

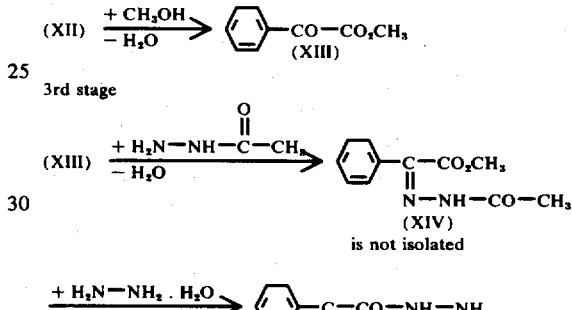

(XIV)

is not isolated $\xrightarrow[- \text{CH}_3\text{OH}]{+ \text{H}_2\text{N}-\text{NH}_2 \cdot \text{H}_2\text{O}}$ ⌬—C—CO—NH—NH$_2$
                                                                  ‖
                                                                  N—NH—CO—CH$_3$
(XV)

4th stage

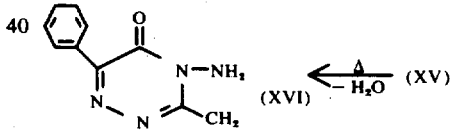

(XVI) $\xleftarrow[- \text{H}_2\text{O}]{\Delta}$ (XV)

This reaction sequence may be effected as follows:

1st stage

At least 200 ml of water were introduced into 1 mole of liquid thioamides (VI B) at a temperature >80° C. 3 moles of 45% strength sodium hydroxide solution were then added slowly at the reflux temperature (about 100° C). The mixture was then neutralized at 20° C and sulfur which had precipitated was filtered off. The filtrate was then strongly acidified with concentrated hydrochloric acid and the ketoacid (XII), which separates out as an oil, was extracted with ethylene chloride. The yield was 90%.

2nd stage

Sulfuric acid (13 ml/mole) and methanol (100 g/mole) were added to the ethylene chloride solution from the 1st stage. The mixture was then allowed to react under reflux for 12 hours. The upper sulfuric acid/water/methanol phase was then separated off; the ethylene chloride solution was extracted by stirring with bicarbonate solution and concentrated by distilling off the solvent. The yield of phenylglyoxyl acid ester (XIII) was 87%.

3rd stage 1 mole of phenylglyoxyl acid ester (XIII) and 1 mole of acetylhydrazine were heated in 760 g of isopropanol for 5 hours under reflux. A little p-toluensulfonic acid was added as the catalyst. The hydrazone (XIV) was obtained as a mixture of isomers, only one isomer crystallizing out. The mixture was therefore worked up without isolating the hydrazone. After the ester had been consumed, hydrazine hydrate was added to this reaction solution and the mixture was kept at 20° C for 5 hours whilst stirring. The reaction mixture was then cooled to 0°–5° C and filtered. The yield of pure hydrazone (XV) was 85%.

4th stage 1,000 g of isopropanol was added to 1 mole of hydrazone (XV) and the mixture was stirred for 24 hours at 100° C in a closed kettle (2-3 atmospheres gauge). It was then filtered at −5° C. 4-Amino-3-methyl-6-phenyl-1,2,4-triazin-5(4H)-one (XVI) of melting point 167°–169° C was obtained in 83% yield.

The process according to the present invention is illustrated by the following preparative examples.

Example 1

Preparation of tert.-butylglyoxyl acid thiodimethylamide

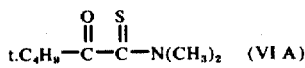

a. On an industrial scale 113 kg (2,500 moles) of dimethylamine were passed into 200 kg of water in a 500 liter kettle. 16 kg (500 moles) of sulfur were then added and the reaction mixture was warmed to 60° to 70° C. 85 kg (500 moles) of α,α-dichloropinacolone were then allowed to run, from a heated bulb, in the course of about 2 hours, into the mixture, at an internal temperature of 60° to 70° C. The mixture was then stirred for a further 2 hours at about 75° C. It was then cooled to 0° C and seed crystals were added, whereupon tert.-butylglyoxyl acid thiodimethylamide crystallized out. The mixture was stirred for a further 1 hour at 0° C and was then filtered through a box suction filter. The product was dried on Leguval sheets in a circulating air drying cabinet at room temperature. 80.0 kg (95% of theory) of tert.-butylglyoxyl acid thiodimethylamide of melting point 40–43° C were obtaind.

b. On a laboratory scale 170 g (1 mole) of dichloropinacolone and 32 g (1 mole) of sulfur were heated to 70° C. 250 g of dimethylamine solution ( ≙ 2.2 moles of dimethylamine) and 180 g of 45% strength sodium hydroxide solution ( ≙ 2 moles of sodium hydroxide were then allowed to run in dropwise, in the course of 30 minutes in each case. Since the reaction was exothermic, slight cooling was required and the temperature had to be kept at about 70° C. After further stirring for a short time, the mixture was cooled to 0° C and seed crystals were added, whereupon tert.-butylglyoxyl acid thiodimethylamide crystallized out. The solid was filtered off and air-dried. 161 g (93% of theory) of tert.-butylglyoxyl acid thiodimethylamide of melting point 40°–43° C were obtained.

Example 2

Preparation of phenylglyoxl acid thiodimethylamide

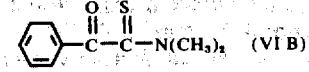

250 g of dimethylamine solution (40% strength in ethanol) ( ≙ 2.2 moles of dimethylamine) and 80 g (2 moles) of sodium hydroxide solution in 450 ml of water were added dropwise in the course of 30 minutes to 64 g (2 moles) of sulfur and 154.6 g (1 mole) of α-chloroacetophenone in 200 ml of water. The reaction proceeded exothermically up to about 60° C. The mixture was stirred at this temperature for 30 minutes. It was then cooled to about 0° C and kept at this temperature for 30 minutes whilst stirring. The solid was filtered off and washed with water. 182 g (94% of theory) of phenylglyoxyl acid thiodimethylamide of melting point 83°–84° C were obtained.

It will be understood that the specification and examples are illustrative but not limitative of the present invention and that other embodiments within the spirit and scope of the invention will suggest themselves to those skilled in the art.

What is claimed is:

1. A process for the preparation of an α-oxothiodimethylamide of the general formula

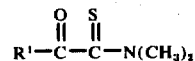

in which
R$^1$ is alkyl or aryl,
which process comprises reacting an α-chloroketone of the general formula

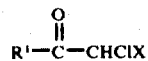

in which
X is hydrogen or chlorine and
R$^1$ is identified as above,
with sulfur and dimethylamine in water at a temperature between 50° and 90° C.

2. A process as claimed in claim 1, in which R$^1$ is an alkyl radical of from 1 to 4 carbon atoms or aryl of from 6 to 10 carbon atoms.

3. A process as claimed in claim 2, in which R$^1$ is a tert.-butyl.

4. A process as claimed in claim 2, in which R$^1$ is phenyl.

5. A process as claimed in claim 1 wherein the reaction is effected at between 60° and 80° C.

6. A process as claimed in claim 1 in which X is chlorine and wherein 1 mole of sulfur and at least 3 moles of dimethylamine are employed per mole of the α-chloroketone.

7. A process as claimed in claim 1 in which X is hydrogen and wherein 2 moles of sulfur and at least 2 moles of dimethylamine are employed per mole of the α-chloroketone.

8. A process as claimed in claim 1 wherein sodium hydroxide solution is additionally used with said dimethylamine.

9. A process for the preparation of tert.-butylglyoxyl acid thiodimethylamide which comprises reacting α,α-dichloropinacolone with sulfur and dimethylamine in water at a temperature of from 50° to 90° C.

10. A process as claimed in claim 9 wherein the reaction temperature is from 60° to 70° C.

11. A process as claimed in claim 9 wherein the mole ratio of said α,α-dichloropinacolone to said dimethylamine is about 1 to 5.

12. A process as claimed in claim 9 wherein roughly equimolar amounts of α,α-dichloropinacolone and sulfur are employed.

* * * * *